United States Patent [19]

Tabor et al.

[11] Patent Number: 4,482,321

[45] Date of Patent: Nov. 13, 1984

[54] ORTHODONTISTS BRACKET REGISTRATION WAFER

[76] Inventors: Sam H. Tabor, 426 Mission Dr., Camarillo, Calif. 93010; Bruce A. Tabor, 619 Del Oro Dr., Ojai, Calif. 93023

[21] Appl. No.: 413,742

[22] Filed: Sep. 1, 1982

[51] Int. Cl.³ .............................................. A61C 9/00
[52] U.S. Cl. ......................................... 433/71; 433/2
[58] Field of Search ............................... 433/6, 71, 70

[56] References Cited

U.S. PATENT DOCUMENTS 2,633,637  4/1953  Lucia .................................... 433/70
4,324,547  4/1982  Arcan et al. ......................... 433/71

Primary Examiner—Robert Peshock
Attorney, Agent, or Firm—William C. Babcock

[57] ABSTRACT

A generally semi-elliptical shaped wafer of a light weight material having upper and lower surfaces that may be pressure gripped between the bracket supporting teeth of an orthodontic patient, with the material being one that permanently deforms when substantial pressure is applied thereto, and as a result each wafer when subjected to such gripping having impressions formed therein that record the relative positions of the brackets and the teeth associated therewith. By using the wafers successively on patient visits to an orthodontist, a permanent record is maintained of the progress being made in straightening and aligning the teeth of each patient, or other corrective orthodontic work. In addition, the impressions of the brackets on the wafer indicate to the orthodontist the extent to which the arch wire must be bent or deformed to exert a desired force on the teeth for further corrective procedures.

4 Claims, 9 Drawing Figures

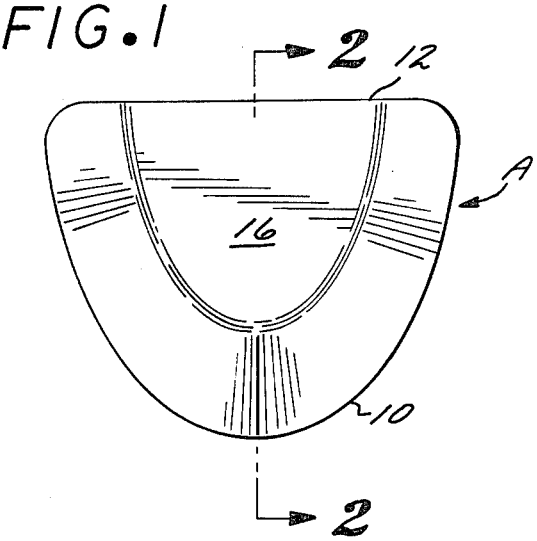
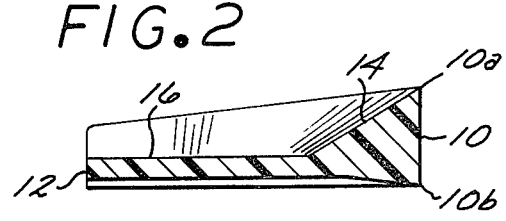
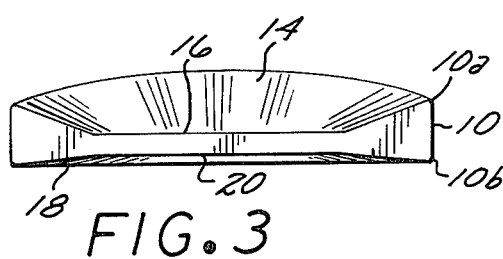
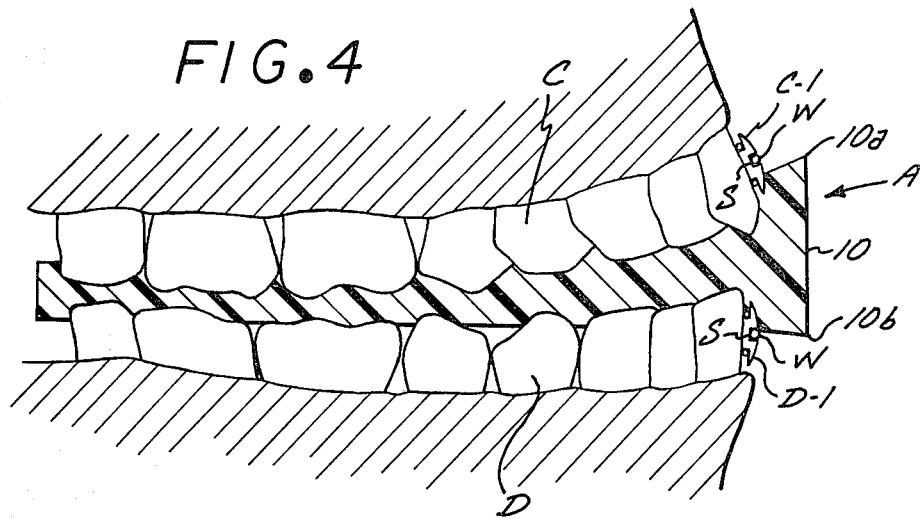
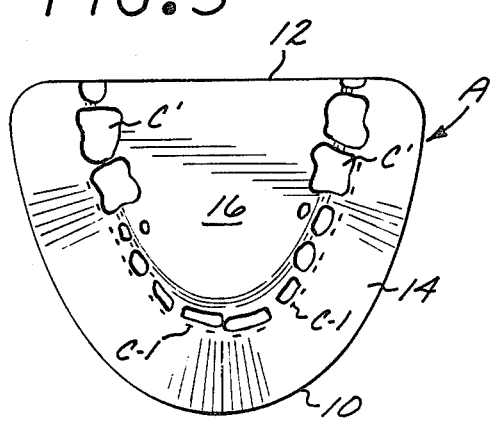
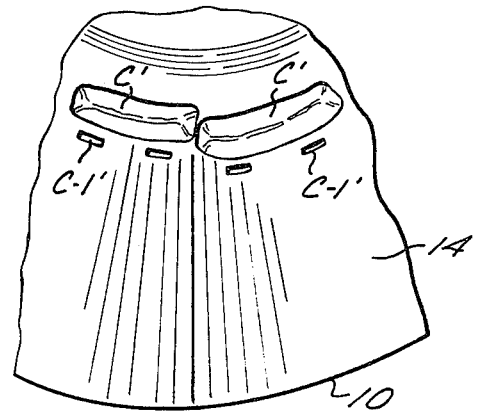

ORTHODONTISTS BRACKET REGISTRATION WAFER

SUMMARY OF THE INVENTION

In carrying out orthodontic work, a series of brackets are secured to either the exterior or interior surface of the teeth on which the work is being performed. Each of the brackets includes a recess that is engaged by an elongate resilient wire, known as an arch wire, that is removably secured to the brackets by means well known in the orthodontic art.

The arch wire when so removably secured to the brackets exerts predetermined tractive tooth positioning forces on the various teeth that have brackets secured thereto. As the orthodontic work progresses, the patient periodically visits the orthodontist, who inspects the degree of repositioning of the teeth, and the arched wire being replaced by a newly bent arch wire that will exert a desired tractive force on the teeth subjected to the orthodontic treatment. The bending of an arch wire to subject the brackets and teeth to desired forces, results in arch wires being successively mounted and demounted from the brackets, and bent a number of times to provide a wire configuration that will exert the desired forces on the teeth under treatment.

The bending of the arch wire in the above described manner is time consuming, and is an inconvenience to both the patient and the orthodontist. By use of the present invention, a light weight wafer is provided that when gripped between the upper and lower sets of teeth of the patient, has impressions of the relative position of the brackets permanently recorded thereon, and these impressions permitting a new arch wire to be bent without being fit onto brackets in the patients mouth.

A major object of the present invention is to provide a light weight wafer of generally semi-elliptical shape that has upper and lower surfaces, with the wafer capable of being removably disposed within the patients mouth between the upper and lower sets of teeth, with the patient instructed to grip the wafer that results in permanent impressions of the brackets being made in the wafer.

Another object of the present invention is to provide an orthodontics accessory in the form of a light weight, generally semi-elliptical wafer, formed from light weight material such as styrafoam in which beads thereof are bonded together, which material is permanently deformable when localized areas are subject to substantial pressure, and the wafer as a result having impressions of the positions of the brackets mounted on the teeth when the wafer is inserted in a patients mouth and gripped between the upper and lower sets of teeth.

Another object of the invention is to provide an orthodontist accessory in the form of a wafer that when gripped between the upper and lower sets of a patients teeth visually and permanently records on the wafer the position of the brackets mounted on the teeth, and the visual records being utilized by the orthodontist or a technician associated with the latter to bend or deform an arch wire to achieve a further repositioning of the teeth by applying a number of predetermined forces on the teeth supported bracket. This objective is achieved without the necessity of bending the arch wire and demounting it in succession from the teeth supporting brackets.

A still further object of the invention is to provide a wafer that may be used to provide a permanent record of the relative positions of the teech and brackets in a patients mouth, and when a succession of such wafers are used on a patient on his periodic visits to an orthodontist providing a permanent record of the progress being made in the orthodontic work by recording the positions of the brackets on the teeth at each visit is made by the patient.

Yet another object of the invention is to provide an orthodontist wafer that permits orthodontic work to be carried out more efficiently by an orthodontist and with less inconvenience to both the orthodontist and the patient.

These and other objects and advantages of the present invention will become apparent from the following description thereof.

BRIEF DESCRIPTION OF THE DRAWINGS

FIG. 1 is a top plan view of a first form of an orthodontist wafer;

FIG. 2 is a longitudinal cross sectional view of the wafer taken on the line 2—2 of FIG. 1;

FIG. 3 is an end elevational view of the wafer;

FIG. 4 is a diagrammatic view illustrating the manner in which the wafer is gripped between the upper and lower sets of teeth in a patients mouth to register the relative positions of the brackets on the patients teeth to one another;

FIG. 5 is a top plan view of the wafer after the same has been used, and having the upper surface permanently deformed by impressions of the teeth and the brackets mounted on the teeth;

FIG. 6 is an enlarged fragmentary view of an upper section of the wafer shown in FIG. 5 in which the configuration of the lower portions of the teeth, and the brackets mounted thereon, are permanently recorded on the wafer in the form of impressions made therein;

DESCRIPTION OF THE PREFERRED EMBODIMENTS

Figure 7:
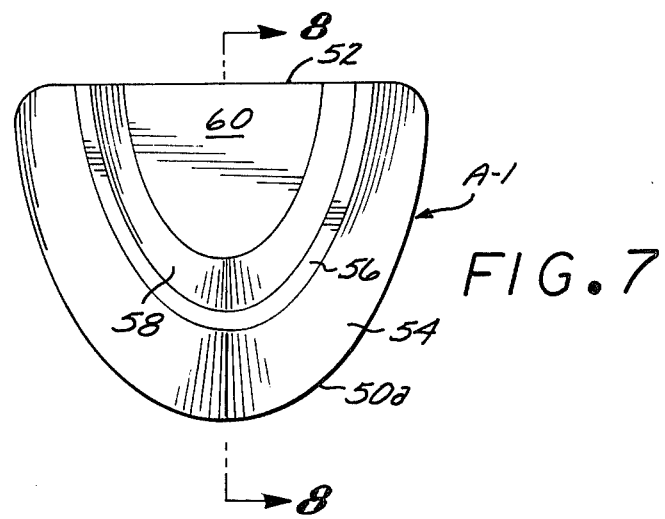
FIG. 7 is a top plan view of a second form of the wafer.

A first form A of a bracket registration wafer for use by an orthodontist is illustrated in FIGS. 1-3 inclusive. The orthodontist wafer A is preferably formed by dry molding of syrafoam beads, preferably of number three density, into the configuration shown in the drawings.

The wafer A is shown in FIG. 4 as being disposed in the mouth of a patient B, and the patient having an upper set of teeth C and lower set of teeth D. The upper set of teeth C is illustrated as having orthodontic brackets C-1 mounted thereon, and the lower set of teeth D having brackets D-1 thereon.

In FIG. 4 it will be seen that the first form of wafer A is inserted in the mouth of the patient B and gripped by the upper and lower sets of C and D respectively, with the teeth and brackets C-1 and D-1 exerting a gripping force on the wafer that results in impressions being made therein that are of a permenant nature. Each of the wafers A as best seen in FIGS. 2 and 3 includes a generally semi-elliptical side wall 10 and a substantially straight rear edge 12. An upper edge 10a of side wall 10 has an upper marginal portion of 14 or the wafer tapering downwardly therefrom, with the marginal portion 14 at the lower extremity developing into a flat upper surface 16.

The side wall 10 has a lower edge 10b from which a lower marginal portion 18 of the wafer tapers upwardly to develop into a flat lower surface 20. The flat upper and lower surfaces 16 and 20 are spaced a relatively small distance from one another, and that distance being only sufficient to render demensional stability to the wafer A both prior to and during use thereof.

Both the brackets C-1 and D-1 as is common with such devices has transverse slots S formed therein that are removably engaged by an arch wire W. The arch wire W by bending or deforming as is conventional in the orthodontic phase of dentistry is bent to exert a tractive force on the brackets C-1 and D-1 that is transmitted to the individual teeth C and D. This tractive force when applied over a prolonged period of time causes relative movement of the teeth C and D to one another to correct deficiencies in the straightness and spacing thereof.

Figure 8:
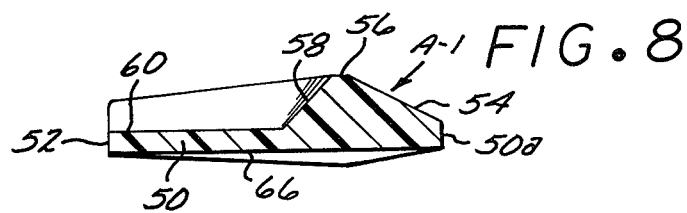
FIG. 8 is a longitudinal cross sectional view of the second form of the wafer taken on the line 8—8 of FIG. 7.
Figure 9:
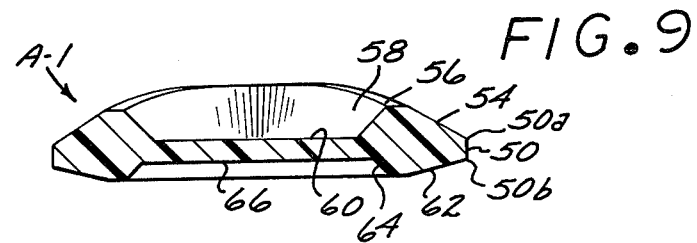
FIG. 9 is an end elevational view of the second form of the wafer.

An alternate form A-1 of the orthodon bracket registration wafer is shown in FIG. 7, 8 and 9. The first alternate form A-1 is preferably formed from the same materials as used in the first form A.

The alternate form A-1 as shown in FIGS. 7–9 inclusive is defined by a semi-elliptical side wall 50 and a rear edge 52. The side wall 50 has an upper edge 50a and lower edge 50b. The upper edge 50a develops into an upwardly and inwardly inclined marginal surface portion 54 that on the inner extremity merges with a flat narrow upper surface 56, which surface 56 develops on the inner extremity into a downwardly inclined wall surface 58. The wall surface 58 at the lower edge thereof merges into a flat upper surface 60 as shown in FIGS. 8 and 9.

The lower edge 50b has a lower marginal surface portion 62 extending inwardly and downwardly therefrom, with the marginal portion on the inner extremity developing into an upwardly and inwardly inclined wall surface 64 that on the inner extremity merges into a lower flat surface 66. The alternate form A-1 is utilized in the same manner as the form A, and is adapted to have impressions of brackets on both the upper and lower sets of teeth of the patient B impressed thereon on the same manner as shown in FIG. 4.

In viewing FIG. 4 it will be apparent that the bracket C-1 and D-1 on the upper and lower sets of teeth C and D will form impressions C-1' as shown in FIG. 6, and the teeth will form impression C' when the first form of wafer A is gripped between the teeth C and D. In the event that the bracket C-1 and D-1 are mounted on the interior surfaces of the teeth which is common in orthodontic practice as of to-day, and impressions C-1' as shown in phantom line in FIG. 6 will be formed inwardly from the impressions C' of the teeth. The use and operation of the orthodontist bracket registration wafer has been described previously in detail and need not be repeated.

What is claimed is:

1. A bracket registration wafer accessory for use by an orthodontist to visually determine the relative positions of the teeth of a patient and brackets mounted on said teeth when the lower edges of said brackets are a substantial distance above the lower extremities of said teeth and provide a permanent record of such positioning, said accessory being a wafer of a generally semi-elliptical shape and of a size to permit the insertion of the wafer into the patients mouth between the upper and lower teeth, said wafer formed from a dimensionally stable but pressure deformable material, said wafer having upper and lower surfaces, said upper surface having a substantially flat central portion that develops into an outwardly disposed semi-elliptical marginal portion that slopes upwardly and outwardly relative to said central portion, said marginal portion of such size that when said wafer is gripped between the upper and lower teeth impressions of the upper teeth will be defined in said marginal portion of said upper surface adjacent said central portion, and said marginal surface portion and said lower surface cooperating to provide a body of said deformable material therebetween of sufficient thickness that when gripped between the upper and lower teeth of the patient relative deep impressions of the patients upper teeth are made in the marginal surface portion and such depth being to the extent that impressions of said brackets secured to said upper teeth are concurrently.

2. A wafer as defined in claim 1, in which said wafer is defined in its entirety by a plurality of dry molded beads of styrafoam, which beads have a density of approximately three.

3. An accessory as defined in claim 1 in which said lower surface is of the same general shape as said upper surface, but with the marginal surface portion of said lower surface sloping downwardly and outwardly and having impressions of the patients lower teeth and any brackets thereon made in said lower marginal surface portion concurrently with the making of said impressions of said upper teeth and brackets thereon in said upper marginal surface portion.

4. A bracket registration wafer assembly as defined in claim 3, in which said wafer is defined in its entirety by dry molded styrafoam beads having a density of approximately three.

* * * * *